US011142736B2

(12) United States Patent
Clark et al.

(10) Patent No.: US 11,142,736 B2
(45) Date of Patent: *Oct. 12, 2021

(54) GAS PERMEABLE MATERIAL

(71) Applicant: Saint-Gobain Performance Plastics Corporation, Solon, OH (US)

(72) Inventors: Sarah Louise Clark, Somerville, MA (US); Natasha Anna Lundgren, Boston, MA (US); Michael John Tzivanis, Chicopee, MA (US); Aijun Zhu, Acton, MA (US)

(73) Assignee: Saint-Gobain Performance Plastics Corporation, Solon, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/928,296

(22) Filed: Jul. 14, 2020

(65) Prior Publication Data

US 2020/0339927 A1    Oct. 29, 2020

Related U.S. Application Data

(63) Continuation of application No. 15/937,434, filed on Mar. 27, 2018, now Pat. No. 10,711,235, which is a continuation of application No. 14/976,372, filed on Dec. 21, 2015, now Pat. No. 9,926,524.

(60) Provisional application No. 62/095,116, filed on Dec. 22, 2014.

(51) Int. Cl.
| B32B 25/08 | (2006.01) |
| C12M 1/04 | (2006.01) |
| C12M 1/00 | (2006.01) |
| B32B 25/14 | (2006.01) |
| B32B 25/20 | (2006.01) |
| B32B 27/30 | (2006.01) |
| B32B 27/32 | (2006.01) |
| B32B 27/36 | (2006.01) |
| B32B 1/02 | (2006.01) |
| B32B 25/12 | (2006.01) |
| B32B 27/18 | (2006.01) |
| B32B 25/16 | (2006.01) |
| B32B 7/08 | (2019.01) |
| B32B 27/28 | (2006.01) |
| B32B 7/12 | (2006.01) |
| B32B 27/24 | (2006.01) |
| B32B 25/18 | (2006.01) |
| B32B 27/08 | (2006.01) |
| B32B 27/40 | (2006.01) |
| B32B 27/34 | (2006.01) |
| B32B 1/08 | (2006.01) |

(52) U.S. Cl.
CPC .............. *C12M 23/24* (2013.01); *B32B 1/02* (2013.01); *B32B 1/08* (2013.01); *B32B 7/08* (2013.01); *B32B 7/12* (2013.01); *B32B 25/08* (2013.01); *B32B 25/12* (2013.01); *B32B 25/14* (2013.01); *B32B 25/16* (2013.01); *B32B 25/18* (2013.01); *B32B 25/20* (2013.01); *B32B 27/08* (2013.01); *B32B 27/18* (2013.01); *B32B 27/24* (2013.01); *B32B 27/28* (2013.01); *B32B 27/281* (2013.01); *B32B 27/283* (2013.01); *B32B 27/285* (2013.01); *B32B 27/286* (2013.01); *B32B 27/288* (2013.01); *B32B 27/30* (2013.01); *B32B 27/302* (2013.01); *B32B 27/304* (2013.01); *B32B 27/306* (2013.01); *B32B 27/308* (2013.01); *B32B 27/32* (2013.01); *B32B 27/322* (2013.01); *B32B 27/34* (2013.01); *B32B 27/36* (2013.01); *B32B 27/365* (2013.01); *B32B 27/40* (2013.01); *C12M 23/20* (2013.01); *C12M 23/26* (2013.01); *B32B 2250/02* (2013.01); *B32B 2270/00* (2013.01); *B32B 2274/00* (2013.01); *B32B 2307/412* (2013.01); *B32B 2307/50* (2013.01); *B32B 2307/5825* (2013.01); *B32B 2307/714* (2013.01); *B32B 2307/724* (2013.01); *B32B 2307/7265* (2013.01); *B32B 2307/73* (2013.01); *B32B 2307/732* (2013.01); *B32B 2439/00* (2013.01); *B32B 2439/46* (2013.01); *B32B 2597/00* (2013.01)

(58) Field of Classification Search
CPC ...... C12M 23/20; C12M 23/24; C12M 23/26; B32B 25/20; B32B 25/08; B32B 27/322
See application file for complete search history.

(56) References Cited

U.S. PATENT DOCUMENTS

| 3,030,290 A | 4/1962 | Ryan et al. |
| 3,255,099 A | 6/1966 | Wolinski |
| 3,274,089 A | 9/1966 | Wolinski |
| 3,274,090 A | 9/1966 | Amborski |

(Continued)

FOREIGN PATENT DOCUMENTS

| EP | 1435261 | 7/2004 |
| WO | 03/008011 | 1/2003 |

(Continued)

OTHER PUBLICATIONS

Albers et al., "Structural and Functional Characteristics of Chimeric Avidins Physically Adsorbed onto Functionalized Polythiophene Thin Films," ACS Applied Materials & Interfaces, 2012, pp. 4067-4077.

(Continued)

*Primary Examiner* — Robert S Jones, Jr.
(74) *Attorney, Agent, or Firm* — McDonnell Boehnen Hulbert & Berghoff LLP

(57) ABSTRACT

The invention describes a gas permeable fluoropolymer and silicone material used in the construction of cell culture bags.

24 Claims, 2 Drawing Sheets

(56) References Cited

U.S. PATENT DOCUMENTS

| | | | |
|---|---|---|---|
| 3,274,091 | A | 9/1966 | Amborski |
| 3,275,540 | A | 9/1966 | McBride |
| 3,284,331 | A | 11/1966 | McBride et al. |
| 3,291,712 | A | 12/1966 | McBride |
| 3,296,011 | A | 1/1967 | McBride et al. |
| 3,391,314 | A | 7/1968 | Carter |
| 3,397,132 | A | 8/1968 | Wolinski |
| 3,485,734 | A | 12/1969 | Pecka |
| 3,507,763 | A | 4/1970 | McBride |
| 3,676,181 | A | 7/1972 | Kowalewski |
| 3,873,423 | A | 3/1975 | Munder et al. |
| 4,549,921 | A | 10/1985 | Wolfe |
| 4,829,002 | A | 5/1989 | Pattillo et al. |
| 4,847,462 | A | 7/1989 | Soodak et al. |
| 4,937,194 | A | 6/1990 | Pattillo et al. |
| 4,945,203 | A | 7/1990 | Soodak et al. |
| 5,225,346 | A | 7/1993 | Matsumiya et al. |
| 5,686,304 | A | 11/1997 | Codner |
| 5,935,847 | A | 8/1999 | Smith et al. |
| 6,060,317 | A | 5/2000 | Malech |
| 6,297,046 | B1 | 10/2001 | Smith et al. |
| 6,638,728 | B1 | 10/2003 | Desai et al. |
| 6,726,979 | B2 | 4/2004 | Friedman et al. |
| 7,316,932 | B2 | 1/2008 | Woodside |
| 7,329,742 | B2 | 2/2008 | Doyle et al. |
| 7,514,075 | B2 | 4/2009 | Hedrick et al. |
| 8,138,289 | B2 | 3/2012 | Kofinas et al. |
| 8,318,438 | B2 | 11/2012 | Vivekananda et al. |
| 8,512,566 | B2 | 8/2013 | Griffin et al. |
| 8,727,132 | B2 | 5/2014 | Miltenyi et al. |
| 8,747,289 | B2 | 6/2014 | Coelho |
| 9,926,524 | B2 * | 3/2018 | Clark .................... B32B 27/281 |
| 10,280,930 | B2 | 5/2019 | Lundgren |
| 10,711,235 | B2 | 7/2020 | Clark et al. |
| 2003/0162190 | A1 | 8/2003 | Gorenstein et al. |
| 2005/0032205 | A1 | 2/2005 | Smith et al. |
| 2009/0239762 | A1 | 9/2009 | Tan et al. |
| 2010/0170632 | A1 | 7/2010 | Gautriaud |
| 2011/0287202 | A1 | 11/2011 | Ichisaka |
| 2012/0142088 | A1 | 7/2012 | Hsiao et al. |
| 2013/0040837 | A1 | 2/2013 | Karp et al. |
| 2013/0109086 | A1 | 5/2013 | Kobayashi et al. |
| 2013/0130361 | A1 | 5/2013 | Okano et al. |
| 2013/0164831 | A1 | 6/2013 | Tanaka et al. |
| 2013/0236335 | A1 | 9/2013 | Nelson et al. |
| 2014/0066281 | A1 | 3/2014 | Weasler et al. |
| 2016/0177246 | A1 | 6/2016 | Lundgren |

FOREIGN PATENT DOCUMENTS

| | | |
|---|---|---|
| WO | 2012031234 | 3/2012 |
| WO | 201207619 | 6/2012 |
| WO | 2013049860 | 4/2013 |
| WO | 2014120344 | 8/2014 |

OTHER PUBLICATIONS

Antharavally et al., "Quantitation of Proteins using a Dye-metal-based Colorimetric Protein Assay," Analytical Biochemistry, No. 385, 2009, pp. 342-345.

Balamurugan et al., "Surface immobilization methods for aptamer diagnostic application," Anal Bioanal Chem, No. 390, 20089, pp. 1009-1021.

Coates, "Interpretation of Infrared Spectra, A Practical Approach," In Encyclopedia of Analytical Chemistry, Chichester: John Wiley & Sons, 2000, pp. 10815-10837.

Drumheiler et al., "Surface Immobilization of Adhesion Ligands for Investigation of Cell-Substreate Interactions," CRC Press LLC, 2003, pp. 9.1-9.14.

Fabre et al., "Immobilization of Double Functionalizied Carbon Nanotues on Glassy Carbon Electrodes for the Electrochemical Sensing of the Biotin-avidin Affinity," Journal of Electroanalytical Chemistry, No. 665, 2012, pp. 90-94.

Gauvreau et al., "Engineering Surfaces for Bioconjugation: Developing Strategies and Quantifying the Extent of the Reactions," Bioconjugate Chem., 2004, ages 1146-1156.

Heikkinen et al., "Covalent Biofunctionalization of Cellulose Acetate with Thermostable Chimeric Avidin," ACS Appl. Mater. Interfaces, No. 3, 2011, pp. 2240-2245.

Lachmann et al., "Surface modification of closed plastic bags for adherent cell cultivation," Eur. Phys. J. Appl. Phys., No. 55, 2011, p. 13812.

McGettrick et al., "A Substrate-Independent Approach for the Surface Immobilization of Oligonucleotides using Aldehyde Functionalized Surfaces," Chem. Vap. Deposition, No. 15, 2009, pp. 123-127.

Ocana et al., "A Comparison of four protocols for the Immobilization of an aptamer on graphite composite electrodes," Microchim Acta, No. 181, 2014, pp. 355-363.

Oh et al., "Surface Modification for DNA and Protein Microarrays," Journal of Integrative Biology, vol. 10, No. 3, 2006, pp. 327-343.

Oreima et al., "Generic Method for Attaching Biomolecules via Avidin-Biotin Complexes Immobilized on Films of Regenerated and Nonofibrillar Cellulose," Biomacromolecules, No. 13, 2012, pp. 2802-2810.

Ozer et al., "New Technologies Provide Quantum Changes in the Scale, Speed, and Success of SELEX Methods and Aptamer Characterization," Molecular Therapy—Nucleic Acids, No. 3, e183, 2014, pp. 1-18.

Ponche et al., "Protein/Material Interfaces: Investigation on Model Surfaces," Journal of Adhe3sion Science and Technology, No. 24, 2010, pp. 2141-2164.

Rabe et al., "Understanding Protein Adsorption Phenomena at Solid Surfaces," Advances in Colloid and Interface Science, No. 162, 2011, pp. 87-106.

Racine et al., "A Versatile Gradient of Biomoloecules for Regulating Cell Behaviour," Journal of Adhesion Science and Technology, No. 24, 2010, pp. 975-992.

Srivastava et al., "Polymer-antibody fragment conjugates for biomedical applications," Progress in Polymer Science, 2014, pp. 308-329.

Sromqvist et al., "Binding of biotin to Streptavidin: A combined fluorescence correlation spectroscopy and time-resolved fluorescence study," The European Physical Journal, 2011, pp. 181-194.

Sun et al., "Oligonucleotide Aptamers: New Tools for Targeted Cancer Therapy," Molecular Therapy-Nucleic Acids, 2014, pp. 1-14.

Tadahiro Ohmi, Ultra-Clean Technology Hnadbook: vol. 1: Ultra-Pure Water, CRC Press, 1993, pp. 497-517.

Tong et al., "Peptide surface modification of poly(tetrafluoroethylene-co-hexafluoropropylene) enhances its interaction with central nervous system neurons," Journal of Biomedical Materials Research, 1998, pp. 85-95.

Vermette et al., "Immobilization and Surface Characterization of Neutravidin Biotin-binding Protein on Different Hydrogel Interlayers," Journal of Colloid and Interface Science, No. 259, 2003, pp. 1326.

Vesel et al., "Adsorption of Protein Streptavidin to the Plasma Treated Surface of Polystyrene," Applied Surface Science, 258, 2012, pp. 5558-5560.

Vesel et al., Immobilization of Protein Streptavidin to the Surface of PMMA Polymer, Vacuum, No. 86, 2012, pp. 773-775.

Xia et al., "Ultra Sensitive Affinity Chromatography on Avidin-functionalized PMMA Microchip for Low Abundant Post-translational Modified Protein Enrichment," Biomedical Microdevices, 2012, pp. 67-81.

Ye et al., "Generating Aptamers by Cell-SELEX for Applications in Molecular Medicine," Int. J. Mol. Sci., No. 13, 2012, pp. 3341-3353.

Yun et al., "Human monocyte/macrophage adhesion and cytokine production on surface-modified poly(tetrafluoroethylene/hexafluoropropylene) polymers, with and without protein preadsorption," Journal of Biomedical Materials Research, vol. 29, 1995, pp. 257-268.

(56) References Cited

OTHER PUBLICATIONS

Zhou et al., "Cell-type-specific, Aptamer-functionalized Agents for Targeted Disease Therapy," Molecular Therapy-Nucleic Acids, 2014, pp. 1-17.

* cited by examiner

GAS PERMEABLE MATERIAL

CROSS REFERENCE TO RELATED APPLICATIONS

This application is a continuation of U.S. patent application Ser. No. 15/937,434, filed Mar. 27, 2018, now U.S. patent Ser. No. 10/711,235, which is a continuation of U.S. patent application Ser. No. 14/976,372, filed Dec. 21, 2015, now U.S. Pat. No. 9,926,524, which claims benefit under 35 U.S.C. § 119(e) to U.S. Ser. No. 62/095,116, entitled "FLUORINATED SILICONE FILM FOR OXYGEN PERMEABLE MATERIAL", filed Dec. 22, 2014, the contents of each of which is incorporated herein by reference in its entirety.

FIELD OF THE INVENTION

The invention relates generally to a gas permeable material and application to a cell culture apparatus and a cell culture method.

BACKGROUND OF THE INVENTION

In vitro cell culture is the complex process by which cells are grown under controlled conditions, generally outside of their natural environment but as close to their natural in vivo conditions as possible. In practice cell culture refers to the culturing of cells derived from multi-cellular eukaryotes, especially animal cells. However, there are also cultures of plants, fungi, insects and microbes, including viruses, bacteria and protista.

In vitro cell culture provides material necessary for research and application in pharmacology, physiology, and toxicology. This includes bioprocessing and cell therapy where cell cultures are necessary.

Cells are grown and maintained at an appropriate temperature and gas mixture in a cell incubator. Typically, mammalian cells are incubated at 37° C. with a pH maintained between 7.2 and 7.4. The pH is typically controlled using a bicarbonate buffering system in the medium, in conjunction with an incubator atmosphere of approximately 5-7% carbon dioxide by volume. The carbon dioxide reacts with the water to form carbonic acid which in turn interacts with bicarbonate ions in the medium to form a buffering system which maintains the pH near physiological levels. Oxygen is essential for cellular metabolism and growth. Culture conditions can vary for each cell type, and variation of conditions for a particular cell type can result in different phenotypes.

A variety of cell types are grown in culture including connective tissue cells, skeletal, cardiac, epithelial cells, neural cells, endocrine cells, immune cells, lymphocytes, melanocytes, and many types of tumor cells. Similarly a variety of media are available depending on the particular growth requirements of the cells and the growth conditions.

Commercially available gas permeable cell culture bags are currently a standard device format used for cell culture. Cell culture bags that are constructed with gas permeable films advantageously provide a large surface area for gas exchange while maintaining a closed system. Disposables also helps reduce the risk of contamination for the cell culture and for the environment.

Cell culture bags are commercially available from OriGen Biomedical Group (OriGen PermaLife™ Bags), Baxter (Lifecell® X-Fold™ related to U.S. Pat. Nos. 4,829,002, 4,937,194, 5,935,847, 6,297,046 B1), Medtronic (Si-Culture™, U.S. Pat. No. 5,686,304), Biovectra (VectraCell™), and American Fluoroseal (VueLife™ Culture Bag System, covered by U.S. Pat. Nos. 4,847,462 and 4,945,203).

Gas permeable films should be selected based on a variety of characteristics including gas permeability, moisture vapor transmission, capacity to be altered for desired cell interaction with cells, optical clarity, physical strength, and the like. A wide variety of information exists that describe the types of gas permeable materials that have been successfully used for cell culture.

Among various kinds of rubbery materials, silicone rubbers are preferable in most cases in respect of their electric properties, low cost, precision moldability and durability in repeated bending and releasing movements.

Silicone films for cell culture bags have high oxygen permeability, good optical clarity, good resistance to puncture, typically do not bind cells, and can be easily fabricated into a wide variety of shapes. Silicone films may be less than about 3 mm, about 2 mm, about 1 mm, or about 0.8 mm in the surface areas where gas transfer is desired. The best selection of material depends on the application.

Fluoropolymer films have desirable characteristics that make them a popular choice for culture bags. Compared to silicone, fluoropolymer films are more biologically, chemically and immunologically inert, as well as being hydrophobic. Fluoropolymer films like FEP (fluorinated ethylene-propylene) do not trigger immune responses in immune cells and progenitor immune cells. However fluoropolymer films are more expensive, less gas permeable then silicone films, and are difficult to adhere to other polymers.

Therefore a need exists which alleviates the disadvantages of using either silicone or fluoropolymer for cell culture bags alone.

BRIEF SUMMARY OF THE INVENTION

In one aspect an oxygen permeable composition is provided. In another aspect a two-part composite having a first layer of elastomer and a second fluid contact layer, wherein the second fluid contact layer has a total organic carbon (TOC) in water of less than 1 $mg/cm^2$. The second fluid contact layer having low TOC can be a fluoropolymer and the first elastomer layer and the second fluoropolymer layer are adhered together. More particularly, the embodiments disclosed herein relate to a fluoropolymer film capable of bonding to the surface of an elastomeric rubber. The fluoropolymer coating exhibits a high bonding strength with or without the use of adhesives.

In another embodiment the outer elastomer layer is natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or mixtures thereof.

In another embodiment the outer elastomer layer is polymethylpentene polymer (PMP).

In another embodiment the oxygen permeable film comprises an outer silicone rubber layer and an inner fluoropolymer layer wherein the inner fluoropolymer layer is coated onto the outer silicone rubber layer.

In another embodiment the silicone rubber of the oxygen permeable film is high consistency rubber (HCR), fluorosilicone rubber (FSR), liquid silicone rubber (LSR), or room temperature vulcanized rubber (RTV), thermoplastic silicone rubber (TPE), platinum cured silicone rubber, or peroxide cured silicone rubber.

In another embodiment the silicone rubber of the oxygen permeable film is thermoset, cured, vulcanized, catalyzed, or injection molded.

In another embodiment the fluoropolymer layer of the film is fluorinated ethylene-propylene (FEP), polytetrafluoroethylene (PTFE), tetrafluoroethylene-perfluoro(propyl vinyl ether) (PFA), polyvinylidene difluoride, hexafluoropropylene/tetrafluoroethylene/vinylidene copolymer (THV), or perfluoro(1-butenyl vinyl ether) homocyclopolymer having functionalized polymer-end groups In another embodiment the elastomer, such as PMP or silicone and fluoropolymer layers of the oxygen permeable film are bonded.

In still another embodiment the adhesion of the elastomer, such as PMP or silicone, and fluoropolymer layers of the oxygen permeable film is by coating, RF welding, ultrasonic welding, hot bar welding, chemical bonding, adhesive bonding, thermal fusion bonding, solvent welding, laser welding, corona discharge, radiation, lamination such as by extreme heat, belt, or melt lamination, etching, plasma treatment, wetting, adhesives, radiation, extrusion, co-extrusion, or combinations thereof.

In another embodiment an oxygen permeable container comprises an outer elastomer layer and an inner fluid contact layer having low TOC. In one aspect the fluid contact layer is a fluoropolymer layer, wherein the inner fluoropolymer layer is adhered to the outer elastomer layer of the container.

In another embodiment the outer elastomer layer of the container is natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or combination thereof.

In another embodiment the outer elastomer layer of the container is polymethylpentene polymer (PMP).

In another embodiment the outer elastomer layer of the container is silicone rubber.

In yet another embodiment the silicone rubber of the oxygen permeable container is high consistency rubber (HCR), fluorosilicone rubber (FSR), liquid silicone rubber (LSR), or room temperature vulcanized rubber (RTV), thermoplastic silicone rubber (TPE), platinum cured silicone rubber, or peroxide cured silicone rubber.

In still another embodiment the silicone rubber of the oxygen permeable container is thermoset, cured, vulcanized, catalyzed, or injection molded.

In another embodiment the fluoropolymer layer of the container is fluorinated ethylene-propylene (FEP), polytetrafluoroethylene (PTFE), polyvinylidenefluoride (PVDF), tetrafluoroethylene-perfluoro(propyl vinyl ether) (PFA), polyvinylidene difluoride (PVF), polychlorotrifluoroethylene (PCTFE), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), hexafluoropropylene/tetrafluoroethylene/vinylidene copolymer (THV), or perfluoro(1-butenyl vinyl ether) homocyclopolymer having functionalized polymer-end groups.

In another embodiment the elastomer layer, such as a silicone or PMP layer, and fluoropolymer layers of the oxygen permeable container are bonded.

In another embodiment the bonding of the oxygen permeable container is by coating, RF welding, ultrasonic welding, hot bar welding, chemical bonding, adhesive bonding, thermal fusion bonding, solvent welding, laser welding, corona discharge, radiation, lamination such as by extreme heat, belt, or melt lamination, etching, plasma treatment, wetting, adhesives, radiation, extrusion, co-extrusion, or combinations thereof.

In another embodiment the oxygen permeable container comprises a bag, flask, or tube.

In another embodiment the oxygen permeable bag, flask, or tube contains a sealable access port.

A method is provided to cultivate cells in an oxygen permeable container. The method includes the steps of a) adding media to the container and b) adding cells to the container wherein the container comprises an outer elastomer layer, an inner fluid contact layer having a TOC in water of less than 1 mg/cm$^2$. In one aspect the inner fluid contact layer is a fluoropolymer layer, wherein the inner fluoropolymer layer is coated onto the outer elastomer layer, and wherein the cells and media are in contact with the inner fluoropolymer layer.

In another embodiment of the method, the outer elastomer layer of the container is natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or combination thereof.

In another embodiment of the method, the outer elastomer layer of the container is polymethylpentene polymer (PMP).

In another embodiment of the method, the outer elastomer layer of the container is silicone rubber.

In yet another embodiment of the method, the silicone rubber of the oxygen permeable container is high consistency rubber (HCR), fluorosilicone rubber (FSR), liquid silicone rubber (LSR), or room temperature vulcanized rubber (RTV), thermoplastic silicone rubber (TPE), platinum cured silicone rubber, or peroxide cured silicone rubber.

In still another embodiment of the method, the silicone rubber of the oxygen permeable container is thermoset, cured, vulcanized, catalyzed, or injection molded.

In another embodiment of the method, the fluoropolymer layer of the container is fluorinated ethylene-propylene (FEP), polytetrafluoroethylene (PTFE), 3M™ Dyneon™ TFM™ modified PTFE, polyvinylidenefluoride (PVDF), tetrafluoroethylene-perfluoro(propyl vinyl ether) (PFA), polyvinylidene difluoride (PVF), polychlorotrifluoroethylene (PCTFE), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), hexafluoropropylene/tetrafluoroethylene/vinylidene copolymer (THV), or perfluoro(1-butenyl vinyl ether) homocyclopolymer having functionalized polymer-end groups.

In another embodiment of the method, the elastomer, e.g., PMP or silicone, and fluoropolymer layers of the oxygen permeable container are bonded.

In another embodiment of the method, the bonding of the oxygen permeable container is by chemical bonding, adhesive bonding, thermal fusion bonding, solvent bonding, laser welding, surface treatment, extrusion, co-extrusion, coating, lamination, belt lamination, coating, or combinations thereof.

In another embodiment of the method, the oxygen permeable container comprises a bag, flask, or tube.

In another embodiment of the method, the oxygen permeable bag, flask, or tube contains a sealable access port.

In another embodiment of the method to cultivate cells the steps a) adding media to the container and b) adding cells to the container are interchangeable.

In another embodiment of the method to cultivate cells the steps a) and b) are followed by incubation of the container.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
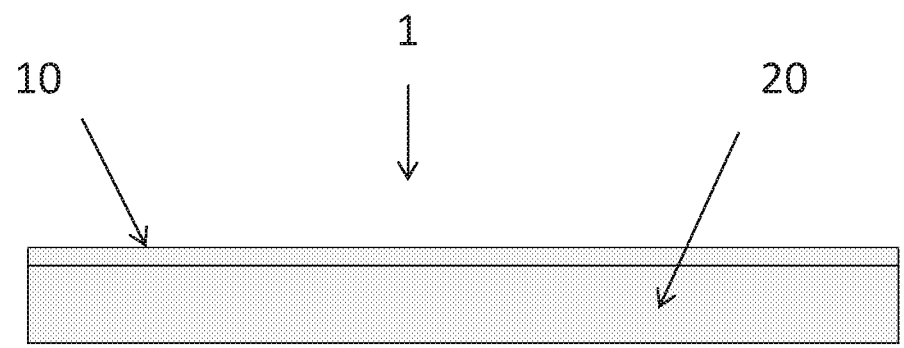
FIG. 1 shows a side view of a fluoropolymer coated elastomer film.

In the specification and in the claims, the terms "including" and "comprising" are open-ended terms and should be interpreted to mean "including, but not limited to . . . ." These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

A combination of the beneficial properties of fluoropolymer and elastomer films described herein applied to cell culture bags is desired in the field and provided herein.

The gas permeable film pertaining to a first aspect described herein comprises a fluoropolymer coated elastomer membrane. Oxygen is necessary for cellular growth in a culture medium and carbon dioxide is necessary for the culture medium to buffer pH. Most normal mammalian cell lines grow well at pH 7.4, and there is very little variability among different cell strains. However, some transformed cell lines have been shown to grow better at slightly more acidic environments (pH 7.0-7.4), and some normal fibroblast cell lines prefer slightly more basic environments (pH 7.4-7.7). Because the pH of the medium is dependent on the delicate balance of dissolved carbon dioxide and bicarbonate, changes in carbon dioxide concentration can alter the pH of the medium. Therefore it is necessary for a fluoropolymer coated elastomer membrane to have good gas permeability to oxygen and carbon dioxide for use in a cell culture bag.

Those skilled in the art will recognize that the gas permeable material should be selected based on a variety of characteristics including flexibility, sealability that ensures airtightness, good clarity that permits the microscopic examination of cell growth, freedom from plasticizers (such as dioctyl phthalate and diisodecyl phthalate) that can be harmful to cells, moisture vapor transmission, capacity to be altered for desired cell interaction with cells, optical clarity, physical strength, and the like.

Elastomers are polymers with viscoelasticity and very weak inter-molecular forces, generally having low Young's modulus and high failure strain compared to other materials. The term elastomers may be used interchangeably with the term rubber, although rubber is preferred when referring to vulcanisates. Elastomers are amorphous polymers constructed from monomers of carbon, hydrogen, oxygen, and/or silicon.

Elastomers comprise unsaturated rubbers that can be cured by sulfur vulcanization, for example natural (NR) and synthetic polyisoprene (IR), polybutadiene (BR), chloropene rubber (CR), butyl rubber (IIR), halogenated butyl rubbers (CIIR, BIIR), styrene-butadiene rubber (SBR), nitrile (NBR) and hydrogenated nitrile rubber (HNBR).

Elastomers comprise unsaturated rubbers that cannot be cured by sulfur vulcanization, for example ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), thermoplastic urethanes (TPUs), including thermoplastic silicones, such as a GENIOMER®, cyclic olefin copolymers, polyolefin elastomers, elastomeric PET, and ethylene-vinyl acetate (EVA).

Thermoplastic polyurethanes (TPUs) are known in the art. Typically, a thermoplastic polyurethane is formed by reacting a polyol with an isocyanate. The overall properties of the polyurethane will depend upon the type of polyol and isocyanate, crystallinity in the polyurethane, the molecular weight of the polyurethane and chemical structure of the polyurethane backbone.

Polyurethanes may be either thermoplastic or thermoset, depending on the degree of crosslinking present. Thermoplastic urethanes (TPUs) do not have primary crosslinking while thermoset polyurethanes have a varying degree of crosslinking, depending on the functionality of the reactants.

Thermoplastic polyurethanes are commonly based on either methylene diisocyanate (MDI) or toluene diisocyanate (TDI) and include both polyester and polyether grades of polyols. Thermoplastic polyurethanes can be formed by a "one-shot" reaction between isocyanate and polyol or by a "pre-polymer" system, wherein a curative is added to the partially reacted polyolisocyanate complex to complete the polyurethane reaction. Examples of some common thermoplastic polyurethane elastomers based on "pre-polymers" are "TEXIN", a tradename of Bayer Materials Science, "ESTANE", a tradename of Lubrizol, "PELLETHANE", a tradename of Dow Chemical Co., and "ELASTOLLAN", a tradename of BASF, Inc.

GENIOMER® thermoplastic silicones include, but are not limited to GENIOMER® 140 Silicone TPE, GENIOMER® 200 Silicone TPE Elastomer (90% polydimethylsiloxane and isocyanate), GENIOMER®, 60 Silicone TPE, GENIOMER® 80 Silicone TPE and GENIOMER® 145 TPE, all of which comprise 90% polydimethylsiloxane and isocyanate.

Polymethylpentene (PMP) is a thermoplastic polymer of methylpentene monomer units and is highly gas permeable and transparent.

Silicone rubber has proven to be a particularly good material for a gas permeable membrane. To guarantee sufficient oxygen and carbon dioxide exchange, the thinnest possible gas exchange membranes are preferred. Membranes with a thickness between 0.1 mm and 1 mm have proven successful.

A silicone membrane may be manufactured economically in any desired shape by injection molding. Silicone is available commercially in many thicknesses, shapes, and specific gas permeabilities. It has high tear resistance and good chemical resistance to the media ordinarily used in cell culturing, and is therefore also especially easy to handle.

The ability to sterilize a gas permeable silicone membrane is also especially advantageous. In particular, it can be effectively sterilized in an autoclave with no substantial changes in shape and can be reused several times.

It is preferred that the silicone rubber used has a leachable and extractable profile as low as possible.

In one embodiment a cell culture container may comprise a single layer of an elastomer, such as a thermoplastic silicone (e.g. GENIOMER® by Wacker Chemie AG, a polydimethylsiloxane/urea copolymer) or a fluoropolymer with TOC and permeability properties as described herein.

It should also be noted that other configurations of thermoplastics (elastomer and non-elastomer) and fluoropolymer configurations could also be used to control the gas permeability of a composite, whilst containing a low TOC fluid contact layer. Control of gas permeability could be for purpose of either creating a high or low gas permeable composite. Examples of thermoplastics elastomers (TPE) include styrene block copolymers (TPE-s), olefins (TPE-o), alloys (TPE-v or TPV), polyurethanes (TPU), copolyesters, and polyamides. Examples of non-elastomer thermoplastics include acrylics, acrylonitrile butadiene styrene (ABS), nylon, polylactic acid (PLA), polybenzimidazole (PBI), polycarbonate (PC), polyether sulfone (PES), polyetherether ketone (PEEK), polyetherimide (PEI), polyethylene (PE), polyphenylene oxide (PPO), polyphenylene sulfide (PPS), polypropylene (PP), polystyrene (PS), and polyvinyl chloride (PVC), ethylene vinyl alcohol (EVOH), as well as any traditionally rigid polymer whose monomer architecture has been modified to reduce crystallinity and increase flexibility.

Microporous, hydrophobic fluoropolymers, for example 3M™ Dyneon™ TFM™ modified PTFE, HTE, or THV, have also proven advantageous as materials for the gas exchange membrane. The hydrophobic nature of fluoropolymers ensures that the gas exchange membrane is impermeable to aqueous media. For a given gas permeability, the required geometry of the gas exchange membrane depends on the gas requirement resulting for cell respiration, and on the partial pressures of the gases involved in cell respiration, especially on the oxygen partial pressure acting on it from outside.

FIG. 1. shows a side view of fluoropolymer coated elastomer film 1. It should be understood that fluoropolymer layer 10 can be disposed upon elastomer layer 20 to form film 1. Fluoropolymer layer 10 can come from a castable solution. Alternatively, the elastomer can also be cast/disposed onto the fluoropolymer layer.

Typically, fluoropolymer layer 10 has a thickness from about 0.001 mm to about 0.7 mm, more particularly from about 0.005 mm to about 0.4 mm and most particularly from about 0.01 mm to about 0.1 mm and all thicknesses in between, including 0.02 mm, 0.03 mm, 0.04 mm, 0.05 mm, 0.06 mm, 0.07 mm, 0.08 mm, and 0.09 mm. In a particular aspect, the fluoropolymer is a FEP layer and the thickness of the fluoropolymer layer is 0.0254 mm or 1 mil.

Elastomer layer 20 generally has a thickness of from about 0.01 mm to about 5 mm, more particularly from about 0.05 mm to about 1 mm and most particularly from about 0.1 mm to about 0.5 mm and all thicknesses in between, including 0.15 mm, 0.2 mm, 0.25 mm, 0.3 mm, 0.35 mm, 0.4 mm, and 0.45 mm. In a particular aspect, the elastomer is a thermoset silicone layer and the thickness of the elastomer layer is 0.127 mm to 0.254 mm or 5 to 10 mil.

The term "castable" is intended to mean a fluoropolymer or non-fluoropolymer capable of being dispersed, dissolved, suspended, emulsified or otherwise distributed in a liquid carrier medium. The liquid carrier medium may be water, organic solvent, or any other liquid in which the polymer may be dispersed, dissolved, suspended, emulsified or otherwise distributed. The liquid carrier medium may be a mixture of suitable liquids. Once distributed within the carrier medium, the polymer and medium is then capable of being deposited or cast upon a supporting material to form a film. The polymer(s) can be mixed with a first carrier liquid. The mixture may comprise a dispersion of polymeric particles in the first carrier liquid, an emulsion of liquid droplets of the polymer, or of a monomeric or oligomeric precursor of the polymer in the first carrier liquid or a solution of the polymer in the first carrier liquid. Additional/equivalent situations that would make a polymer "castable" would be if it is heated above its melting point or processed in a liquid state and then cured by UV, IR, initiatiors, or ebeam so that it becomes solid.

The castable polymer(s) may also be a monomeric or oligomeric precursor of the polymer distributed within a carrier liquid. Most commonly castable compositions are emulsions or dispersions in aqueous media.

The choice of the first carrier liquid is based on the particular polymer and the form in which the material is to be introduced to the casting composition of the present invention. If a solution is desired, a solvent for the particular fluoropolymer is chosen as the carrier liquid. Suitable carriers include, for example, DMAC, NMP, glycol ethers, or water and the like. If a dispersion is desired, then a suitable carrier is one in which the polymer is not soluble. An aqueous solution would be a suitable carrier liquid for a dispersion of polymer particles.

Most commonly castable compositions are emulsions or dispersions in aqueous media. Surfactants can be used to prepare a dispersion in an amount effective to modify the surface tension of the carrier liquid. Suitable surfactant compounds include ionic surfactants, amphoteric, cationic and nonionic surfactants.

Fluoropolymers are generally selected as the fluid contact layer because of their hydrophobicity and because they are biologically, chemically and immunologically inert.

The phrase "fluoropolymer" is known in the art and is intended to include, for example, fluorinated ethylene-propylene (FEP), polytetrafluoroethylene (PTFE), polyvinylidenefluoride (PVDF), polychlorotrifluoroethlylene (PCTFE), polyvinylfluoride (PVF), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), tetrafluoroethylene-perfluoro(alkyl vinyl ether) copolymers (e.g., PFA; tetrafluoroethylene-perfluoro(propyl vinyl ether), polyvinylidene difluoride, hexafluoropropylene/tetrafluoroethylene/vinylidene copolymers (THV), and mixtures thereof.

The phrase "fluoropolymer" also includes amorphous polymers which are non-crystalline when measured by DSC, or whose heat of melting is less than 2 J/g. These include copolymers of TFE with functional or non-functional monomers such as fluoroolefins having 2-8 carbon atoms and fluorinated alkyl vinyl ether in which the alkyl group contains 1 or 3 to 5 carbon atoms. Examples of the non-functional monomers include hexafluoropropylene (HFP), chlorotrifluoro ethylene (CTFE), PEVE, PMVE and perfluoro-(propylene vinyl ether) (PPVE). Functional monomers include perfluoroethyl vinyl ether (EVE), $CF_2CFOCF_2CFCF_3OCF_2CF_2COOCH_3$ (EVE-carbamate), $CF_2CFOCF_2CFCF_3OCF_2CF_2SO_2F$ (PSEPVE), $CF_2CFOCF_2CFCF_3OCF_2CF_2CN$ (8CNVE), $N_3(CF_2CFOCF_2CFCF_3OCF_2CF_2)_3$ (EVE-triazine), $CF_2CFOCF_2CFCF_3OCF_2CF_2CN$ (EVE-CN), $CF_2CFOCF_2CFCF_3OCF_2CF_2$ $CH_2OH$ (EVE-OH), $CF_2CFOCF_2CFCF_3OCF_2CF_2CH_2PO_2(OH)_2$(EVE-P) $CF_2CFOCF_2CFCF_3OCF_2CF_2CH_2COOH$ (EVE-COOH), and 2,2-bistrifluoromethyl-4,5-difluoro-1,3-dioxole (PDD).

Commercially available amorphous fluoropolymer materials include those from DuPont, Wilmington, Del.: TEFLON® SF60 (TFE/PMVE/PEVE, DuPont, Wilmington Del.), TEFLON® SF61 (TFE/PMVE/PEVE/EVE-P), TEFLON® SF50 (TFE/HFP), Teflon® AF 1600 (PDD/TFE), and TEFLON® AF2130 (PDD/CTFE); from Asahi Corporation of Tokyo, Japan: CYTOP® (CYTOP type A, CYTOP type M, CYTOP type S, or CYTOP NM); from MY Polymers Corporation of Rehovot, Israel (MY-133); or from Nusil Corporation of Carpinteria, Calif. (LS-233).

The fluoropolymer solutions may be applied by common coating methods, including but not limited to spray application, dip coating, brushing, or extrusion/injection molding.

CYTOP® is a perfluoro(1-butenyl vinyl ether) homocyclopolymer containing functionalized end groups. It exists as an amorphous resin and is available in a variety of concentrations in perfluorinated solvents and select non-fluoro solvent systems. For example: 0.1 to 1% in 9:5 isopropyl alcohol/isobutyl acetate.

CYTOP type A contains a carboxyl polymer-end group and CYTOP type M contains an amino-silane polymer-end group. Either fluoropolymer can be used with promoters, special primers, or a silane coupling agent for application as a plastic coating. CYTOP type S contains perfluoro polymer-end group for non-adhesion UV resistance and high transparency.

The silicone rubber formulation includes a silicone polymeric matrix. The polymeric matrix may be formed, for example, using a non-polar silicone polymer. The silicone polymer may, for example, include polyalkylsiloxanes, such as silicone polymers formed of a precursor, such as dimethylsiloxane, diethylsiloxane, dipropylsiloxane, methylethylsiloxane, methylpropylsiloxane, or combinations thereof. In a particular, the polyalkylsiloxane includes a polydialkylsiloxane, such as polydimethylsiloxane (PDMS). In general, the silicone polymer is non-polar and is free of halide functional groups, such as chlorine and fluorine, and of phenyl functional groups.

Functionalized polyorganosiloxanes include polydimethylsiloxanes which are endblocked by vinyldimethylsiloxy groups at both ends, dimethyl siloxane-vinylmethylsiloxane copolymers which are endblocked by vinyldimethylsiloxy groups at both ends, and dimethylsiloxane-methylphenyl siloxane copolymers which are endblocked by vinyldimethylsiloxy groups at both ends.

The silicone rubber may comprise a platinum catalyzed liquid silicone rubber (LSR) or a high consistency gum rubber (HCR). The silicone rubber may also comprise a peroxide catalyzed silicone rubber (LSR) or a high consistency gum rubber (HCR). For example, Saint-Gobain produces medical products made from SILMEDIC®, a peroxide based silicone. An example of the silicone rubber as an HCR is GE 94506 HCR available from GE Plastics. Examples of LSR include Wacker 3003 by Wacker Silicone of Adrian, Mich. and Rhodia 4360 by Rhodia Silicones of Ventura, Calif.

In one aspect of the invention, when the silicone rubber is employed as a base rubber, the composition of fluoropolymer coating may contain a reactive compound which binds with the silicone rubber. Examples of the reactive compounds that bind to silicone rubber include hydrocarbon silicon-containing compounds which are particularly preferred.

Examples of such silicon-containing compounds include compounds having a siloxane bond, silane coupling agents having an alkoxysilyl group, functional silanes having a chlorosilyl group or silazane, amino-silane, and silylating agents. Of these, compounds having a siloxane bond, and silane coupling agents having an alkoxysilyl group are preferred. Examples of such compounds having a siloxane bond include end-modified dimethylsiloxanes, condensation-type or addition-type liquid silicones, silicate salts, and acrylic silicone polymers.

An example of a fluoropolymer having an amino-silane end modification is CYTOP type M. Similarly, an example of a fluoropolymer having a carboxyl group end modification is CYTOP type A. Either may be mixed with or without a coupling agent and bond directly or indirectly via coupling agent with a silicone rubber. Chemical bonding may occur by condensation, alkylation, amidation, silylation, etherification, or through a coupling agent by any bonding combination thereof. For example, a coupling agent that may be used with silicone rubber is an isocyanate compound that reacts with hydroxyl, amino, or sulfur groups. After formation of a chemical bond between the fluoropolymer and the silicone rubber, adhesion will be achieved and the composite gas permeable membrane will have a higher strength with minimal leaching. Either CYTOP type A or CYTOP type M after hydrolysis may also adhere to silicone rubber through hydrogen bonding.

Bonding of the elastomer layer and fluoropolymer layers together may also be accomplished by laser welding, surface treatment, radiation, extrusion, co-extrusion, coating, lamination, wetting, adhesives, or combinations thereof. Preferred methods of surface treatment include C-treatment (Saint-Gobain Performance Plastics Corporation, U.S. Pat. No. 6,726,979), corona discharge, plasma treatment, etching, or combinations thereof. Surface treatments may also involve chemical treatment with additives or primers that can be used alone or in conjunction with the other disclosed treatment methods.

In a preferred aspect, the fluoropolymer layer is C-treated FEP that has also been primed and coated with LSR silicone by extrusion.

The layers may also be prelaminated together similar to that described for LIGHTSWITCH® Complete product (Saint-Gobain Performance Plastics Corporation, Valley Forge, Pa.).

Total Organic Carbon (TOC) is the amount of carbon bound in an organic compound and is often used as a non-specific indicator of pharmaceutical manufacturing equipment, among other things. TOC is utilized as a process control attribute in the biotechnology industry to monitor the performance of unit operations that employ purification and distribution systems.

In specific embodiments, TOC may be measured according to US Pharmacopeia (USP) 643 and with equipment that utilizes a high temperature wet oxidation reaction of UV-promoted chemical oxidation (Ultra-Clean Technology Handbook: Volume 1: Ultra-Pure Water, Ohmi, Tadahiro; CRC Press, 1993, pp. 497-517). Purified water is placed in contact with the polymer for 24 hours at 70° C., for example at a ratio of 3 $cm^2$ of article surface area to 1 mL of water. The water is removed from contact with the polymer and tested in a TOC analyzer. A suitable piece of equipment is a TEKMAR DOHRMANN Model Phoenix 8000 TOC analyzer.

In particular embodiments, TOC may be measured for a container employed in a system of the disclosure including, for example by extraction from an internal surface area of the container (with results reflected as $mg/cm^2$ are for the TOC per square centimeter of the internal area). In specific embodiments, and merely as an example, the container may be extracted in purified water 70±2° C. for 24±2 hours. The extract may be analyzed for TOC by converting TOC to carbon dioxide by acidification and chemical wet oxidation with sodium persulfate, for example. The carbon dioxide liberated from the container may be measured using an infrared detector. An example of an extraction ratio for a FEP container is 3 $cm^2/mL$ (a typical extraction ratio). For some containers (such as FEP bags), no dilution is required because the level of TOC is less than the upper limit of a calibration curve, whereas for other embodiments (such as silicone tubing), dilution is required because of the levels of the TOC detected in the extract.

An example of TOC for a FEP container is 0.145 mg/L (0.00005 $mg/cm^2$ or 0.001 mg/g). For embodiments that employ silicone tubing, extraction ratios may be 14.6 $cm^2/mL$ (such as for Biosil) or may be 15.9 $cm^2/mL$ (such as for SR139), and an example of TOC for silicone Biosil tube is 302 mg/L (0.021 $mg/cm^2$ or 0.023 mg/cm), and an example of TOC for silicone SR139 tubing is 120 mg/L (0.008 $mg/cm^2$ or 0.0009 mg/cm). In at least certain silicone tubing embodiments, the samples may be diluted, as the volume and concentration of the extraction cause the value to be above the maximum detection of the machine. The dilution and different extraction ratio requires the comparison of these samples with the bag samples to be made on the weight/area value basis instead.

One of skill in the art recognizes that TOC values may be characterized in weight/volume. However, persons of skill in the art acknowledge that ratios for the container (particularly a FEP bag material) vs. ratios for silicone tubing are distinguishable; silicone tubing values can only be considered on a $mg/cm^2$ starting basis, as this value is independent of extraction ratio/dilution. One of skill in the art can calculate a "normalized" weight/volume ratio using a weight/area result as a basis and assuming a standard 3 $cm^2/mL$ extraction ratio (as an example) in order to compare values on a weight/volume value.

In specific embodiments, the TOC of thermoplastic elastomers (TPE) is 0.002 $mg/cm^2$ (0.032 mg/g or 5.88 mg/mL). In certain embodiments, the TOC of FEP is 0.00005 $mg/cm^2$ of interior wetted surface of an article (0.001 mg/g or 0.145 mg/mL of article). In specific embodiments, the TOC of silicone is 0.021 $mg/cm^2$ or 63 mg/mL on interior wetted surface of an article. In a specific embodiment, a TOC for a PMP film is 0.07 ppm (0.00001 $mg/cm^2$).

In specific embodiments, the TOC of fluorinated ethylene propylene (FEP) is 0.00005 $mg/cm^2$ (0.001 mg/g); the TOC of silicone materials, such as silicone tubing, is 0.021 $mg/cm^2$ (0.023 mg/cm) and 0.008 $mg/cm^2$ (0.009 mg/cm); the TOC for a historically used cell culture bag is 0.002 $mg/cm^2$ (0.032 mg/g).

One of skill in the art recognizes that TOC values may be compared across different extraction ratios/dilutions if $mg/cm^2$ units are employed. If units are mg/L, an extraction ratio must be known. A conversion may occur as follows: the machine outputs a value in mg/L, dilution is factored in, and then this number is converted to $mg/cm^2$ using the surface area and total volume to extract. An example for Silicone Biosil is provided: Silicone Biosil Sample: 302 mg/L*1 L/1000 mL*23.7 mL/347 $cm^2$=0.021 $mg/cm^2$ In a particular embodiments, TOC is compared in $mg/cm^2$ units because the extraction ratio or any dilution is not needed.

Below is an example of TOC calculation on a Silicone Tube Biosil sample and on Silicone Tube SR139 sample.

| | Test Article Extraction | | |
|---|---|---|---|
| Sample | Internal Surface Area ($cm^2$) | Length (cm) | Volume of Purified Water (mL) |
| Silicone Tube Biosil Sample | 347 | 314 | 23.7 |

-continued

Test Article Extraction

| Sample | Internal Surface Area (cm²) | Length (cm) | Volume of Purified Water (mL) |
|---|---|---|---|
| Silicone Tube SR139 Sample | 342 | 295 | 21.5 |

Results for TOC Analysis

| Sample | mg/L | mg/cm² | mg/cm | Detection Limit (mg/L) |
|---|---|---|---|---|
| Silicone Tube Biosil Sample | 302 | 0.021 | 0.023 | 0.1 |
| Silicone Tube SR139 Sample | 120 | 0.008 | 0.009 | 0.1 |

Below is an example of TOC calculation on a FEP bag and on a single layer bag mostly composed of a SEBS (styrene block copolymer) but also may contain EVA and PP):

Test Article Extraction

| Sample | Internal Surface Area (cm²) | Weight (g) | Volume of Purified Water (mL) |
|---|---|---|---|
| FEP Bag | 650 | 30.9 | 217 |
| SEBS Bag | 362.9 | 22.5 | 121 |

Results for TOC Analysis

| Sample | mg/L | mg/cm² | mg/g | Detection Limit (mg/L) |
|---|---|---|---|---|
| FEP Bag | 0.145 | 0.00005 | 0.001 | 0.1 |
| SEBS Bag | 5.88 | 0.002 | 0.032 | 0.1 |

In specific embodiments, a container comprises an inner surface comprising a polymer having a total organic carbon (TOC) in water of less than 1 mg/cm², 0.9 mg/cm2, 0.8 mg/cm², 0.7 mg/cm², 0.6 mg/cm², 0.5 mg/cm², 0.4 mg/cm², 0.3 mg/cm², 0.2 mg/cm², 0.1 mg/cm², 0.09 mg/cm², 0.08 mg/cm², 0.07 mg/cm², 0.06 mg/cm², 0.05 mg/cm², 0.04 mg/cm², 0.03 mg/cm², 0.02 mg/cm², 0.01 mg/cm², 0.009 mg/cm², 0.008 mg/cm², 0.007 mg/cm², 0.006 mg/cm², 0.005 mg/cm², 0.004 mg/cm², 0.003 mg/cm², 0.002 mg/cm², 0.001 mg/cm², and so forth, or is nondetectable.

In particular embodiments, the TOC in water is less than an amount in a range from 0.001 mg/cm² to 0.1 mg/cm², 0.001 mg/cm² to 0.095 mg/cm², 0.001 mg/cm² to 0.075 mg/cm², 0.001 mg/cm² to 0.05 mg/cm2, 0.001 mg/cm² to 0.01 mg/cm2, 0.001 mg/cm² to 0.005 mg/cm², or 0.001 mg/cm² to 0.025 mg/cm². In particular embodiments, the TOC in water is less than an amount in a range from 0.01 mg/cm² to 0.1 mg/cm², 0.01 mg/cm² to 0.075 mg/cm², 0.01 mg/cm² to 0.05 mg/cm², or 0.01 mg/cm² to 0.025 mg/cm². In particular embodiments, the TOC in water is less than an amount in a range from 0.05 mg/cm² to 0.1 mg/cm², 0.05 mg/cm² to 0.09 mg/cm², 0.05 mg/cm² to 0.075 mg/cm², or 0.05 mg/cm² to 0.06 mg/cm² In particular embodiments, the TOC in water is less than an amount in a range from 0.005 mg/cm² to 0.1 mg/cm², 0.005 mg/cm² to 0.095 mg/cm², 0.005 mg/cm² to 0.075 mg/cm², 0.005 mg/cm² to 0.05 mg/cm², 0.005 mg/cm² to 0.025 mg/cm², or 0.005 mg/cm² to 0.01 mg/cm².

The materials used in the oxygen permeable films of the current embodiments may have a defined permeability. The permeability of the oxygen permeable elastomer films is at least 100 cc/m² per day, preferably at least 500 cc/m² per day, preferably at least 1000 cc/m² per day, preferably at least 1500 cc/m² per day, and most preferably at least 2000 cc/m² per day and even more preferably at least 2200 cc/m² per day. The permeability of the oxygen permeable elastomer fluoropolymer composite films is at least 100 cc/m² per day, preferably at least 500 cc/m² per day, preferably at least 1000 cc/m² per day, preferably at least 1500 cc/m² per day, and most preferably at least 2000 cc/m² per day and even more preferably at least 2200 cc/m² per day. Oxygen permeability is measured with a MOCON Ox-tran 2/21H Oxygen Analyzer, following ASTM D3985, at 25° C. In another aspect of film permeablility, normalized units (cc-mm/m²-day) can be used to show a film of any thickness. For example, the converted range for a 5 mil film would be from about 12.7 cc-mm/m²-day to at least about 279 cc-mm/m²-day at a temperature of 25° C. The permeability of the contruct/composite can stay in cc/m² terms as it would be comprised of two layers.

Figure 2:
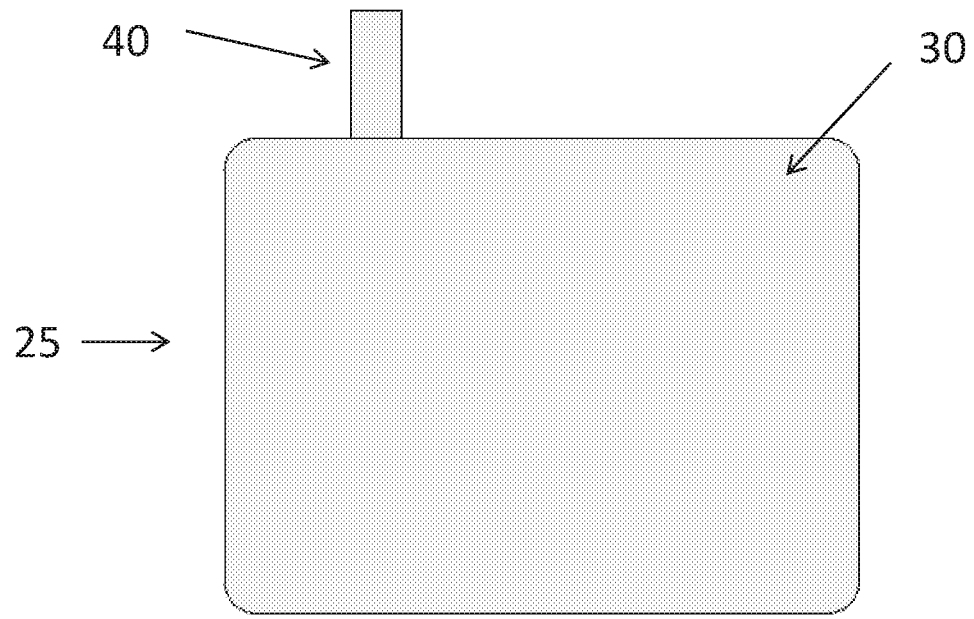
FIG. 2 shows a fluoropolymer coated elastomer culture container.

FIG. 2. is a view of a fluoropolymer coated elastomer cell culture container 25. Fluoropolymer layer 10 (not shown) comprises the inner layer of film 1 that is in contact with the cell culture. Fluoropolymer coated elastomer cell culture container 25 comprises at least one fluorinated elastomer film 1 bonded to form a cell culture compartment 30 which is also bonded to at least one sealable access port 40 that allows access to the interior of the container. Fluoropolymer coated elastomer cell culture container 25 comprises a cell culture compartment 30 which may be a bag, flask, or tube that comprises a closed system that also contains a least one sealable access port 40.

Bonding of film 1 to form cell culture container 30 and bonding of access port 40 to the formed cell culture container 30 each individually, are accomplished by RF welding, ultrasonic welding, hot bar welding, chemical bonding, adhesive bonding, thermal fusion bonding, solvent welding, laser welding, corona discharge, radiation, lamination such as by extreme heat or melt lamination, etching, plasma treatment, wetting, adhesives, radiation, extrusion, co-extrusion, or combinations thereof. Preferred methods of surface treatment include C-treatment (Saint-Gobain Performance Plastics Corporation, U.S. Pat. No. 6,726,979), corona discharge, plasma treatment, etching, or combinations thereof. Surface treatments may also involve chemical treatment with additives or primers that can be used alone or in conjunction with the other disclosed treatment methods. Bonding of access port 40 may occur before, after, or during formation of cell culture container 30.

Cell culture container 30 comprises at least one access port 40 that allows access to the interior of the container. Access port 40 may contain a sealable lid or screw cap, a puncturable material or septa, or a valve assembly to permit access by a tube or syringe. A disposable sensor to measure pH/DO can also be included in the container to monitor cell culture conditions.

The location of the access port(s) is not restricted to the current configuration and a port may be positioned for convenience of use or manufacture. The access port(s) comprise fluoropolymer tubes that are attached to the composite container by RF welding, ultrasonic welding, hot bar welding, chemical bonding, adhesive bonding, thermal fusion bonding, solvent welding, laser welding, corona discharge, radiation, lamination such as by extreme heat or melt lamination, etching, plasma treatment, wetting, adhesives, radiation, co-extrusion, or combinations thereof.

Cell culture container 30 volumes may range from 1 mL to 50 L, 50 mL to 10 L, but preferably 50 mL to 1 L.

Suitable growth media include, for example a nutrient or Lysogeny broth with added hormones and/or growth factors.

Suitable cells include, for example connective tissue cells, skeletal cells, cardiac cells, epithelial cells, neural cells, endocrine cells, immune cells, lymphocytes, melanocytes, tumor cells, or mixtures thereof.

In one embodiment, in a first paragraph (1), the present invention provides an oxygen permeable film comprising a first elastomer layer; and a second fluid contact layer having a total organic carbon (TOC) in water of less than 1 mg/cm$^2$.

2. The film according to paragraph 1, wherein the second fluid contact layer is a fluoropolymer layer, and wherein the first elastomer layer and second fluoropolymer layer are adhered together.

3. The film according to paragraph 1 or 2, wherein the first elastomer layer comprises natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or mixture thereof.

4. The film according to paragraph 1 or 2, wherein the first elastomer layer is polymethylpentene polymer (PMP).

5. The film according to paragraph 1 or 2, wherein the first elastomer layer is silicone rubber.

6. The film according to paragraph 5, wherein the silicone rubber is high consistency rubber (HCR), fluorosilicone rubber (FSR), liquid silicone rubber (LSR), room temperature vulcanized rubber (RTV), thermoplastic silicone rubber (TPE), platinum cured silicone rubber, or peroxide cured silicone rubber.

7. The film according to paragraph 6, wherein the silicone rubber is thermoset, cured, vulcanized, catalyzed, or injection molded.

8. The film according to any one of paragraphs 2 to 7, wherein the second fluoropolymer layer is fluorinated ethylene-propylene (FEP), polytetrafluoroethylene (PTFE), polyvinylidenefluoride (PVDF), tetrafluoroethylene-perfluoro(propyl vinyl ether) (PFA), polyvinylidene difluoride (PVF), polychlorotrifluoroethlylene (PCTFE), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), hexafluoropropylene/tetrafluoroethylene/vinylidene copolymer (THV), or perfluoro(1-butenyl vinyl ether) homocyclopolymer having functionalized polymer-end groups 9. The film according to any one of paragraphs 2 to 8, wherein the first elastomer layer and the second fluoropolymer layer are adhered together by bonding.

10. The film according to paragraph 9, wherein the bonding is by chemical bonding, adhesive bonding, thermal fusion bonding, solvent bonding, laser welding, surface treatment, extrusion, co-extrusion, coating, lamination, or combinations thereof.

11. An oxygen permeable container comprising an outer elastomer layer; and an inner fluid contact layer having a total organic carbon (TOC) in water of less than 1 mg/cm$^2$.

12. The container according to paragraph 11, wherein the fluid contact layer is a fluoropolymer layer, and wherein the inner fluoropolymer layer is adhered to the outer elastomer layer of the container.

13. The container according to paragraph 11 or 12, wherein the outer elastomer layer comprises natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), cyclic olefin copolymers, polyolefin elastomers, elastomeric PET, or mixtures thereof.

14. The container according to paragraphs 11 or 12, wherein the outer elastomer layer is polymethylpentene polymer (PMP).

15. The container according to paragraph 11 or 12, wherein the outer elastomer layer is silicone rubber.

16. The container according to paragraph 15, wherein the silicone rubber is high consistency rubber (HCR), fluorosilicone rubber (FSR), liquid silicone rubber (LSR), or room temperature vulcanized rubber (RTV), thermoplastic silicone rubber (TPE), platinum cured silicone rubber, or peroxide cured silicone rubber.

17. The container according to paragraph 16, wherein the silicone rubber is thermoset, cured, vulcanized, catalyzed, or injection molded.

18. The container according to any one of paragraphs 12 to 17, wherein the inner fluoropolymer layer is fluorinated ethylene-propylene (FEP), polytetrafluoroethylene (PTFE), polyvinylidenefluoride (PVDF), tetrafluoroethylene-perfluoro(propyl vinyl ether) (PFA), polyvinylidene difluoride (PVF), polychlorotrifluoroethlylene (PCTFE), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), hexafluoropropylene/tetrafluoroethylene/vinylidene copolymer (THV), or perfluoro(1-butenyl vinyl ether) homocyclopolymer having functionalized polymer-end groups.

19. The container according to any one of paragraphs 12 to 18, wherein the outer elastomer layer and the inner fluoropolymer layer are adhered together by bonding.

20. The container according to paragraph 19, wherein the bonding is by chemical bonding, adhesive bonding, thermal fusion bonding, solvent bonding, laser welding, and surface treatment, extrusion, co-extrusion, coating, lamination, or combinations thereof.

21. The container according to any one of paragraphs 11 to 20, wherein the container comprises a bag, flask, or tube.

22. The container according to paragraph 21, wherein the bag, flask, or tube contains at least one sealable access port.

23. A method to cultivate cells in an oxygen permeable container comprising the steps of: a) adding media to the container; and b) adding cells, optionally with media, to the container, wherein the container comprises an outer elastomer layer, and an inner fluid contact layer having a total organic carbon (TOC) in water of less than 1 mg/cm$^2$.

24. The method according to paragraph 23, where the inner fluid contact layer is a fluoropolymer layer, and wherein the inner fluoropolymer layer is adhered to the outer elastomer layer of the container.

25. The method according to paragraph 23 or 24, wherein the outer elastomer layer is natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR) and hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), cyclic olefin copolymers, polyolefin elastomers, elastomeric PET, and ethylene-vinyl acetate (EVA).

26. The method according to paragraph 23 or 24, wherein the outer elastomer layer is polymethylpentene polymer (PMP).

27. The method according to paragraph 23 or 24, wherein the outer elastomer layer is silicone rubber.

28. The method according to paragraph 27, wherein the silicone rubber is high consistency rubber (HCR), fluorosilicone rubber (FSR), liquid silicone rubber (LSR), or room temperature vulcanized rubber (RTV), thermoplastic silicone rubber (TPE), platinum cured silicone rubber, or peroxide cured silicone rubber.

29. The method according to paragraph 28, wherein the silicone rubber is thermoset, cured, vulcanized, catalyzed, or injection molded.

30. The method according to one of any paragraphs 24 to 29, wherein the inner fluoropolymer layer is fluorinated ethylene-propylene (FEP), polytetrafluoroethylene (PTFE), 3M™ Dyneon™ TFM™ modified PTFE, polyvinylidenefluoride (PVDF), tetrafluoroethylene-perfluoro(propyl vinyl ether) (PFA), polyvinylidene difluoride (PVF), polychlorotrifluoroethlylene (PCTFE), tetrafluoroethylene/hexafluoropropylene/ethylene copolymer (HTE), chlorotrifluoroethylene/vinylidenefluoride copolymer, chlorotrifluoroethylene/hexafluoropropylene, ethylene/chlorotrifluoroethylene copolymers (ECTFE), ethylene/trifluoroethylene copolymers, ethylene/tetrafluoroethylene copolymers (ETFE), tetrafluoroethylene/propylene copolymers (TFE/P), tetrafluoroethylene/hexafluoropropylene copolymers (FEP/HFP), hexafluoropropylene/tetrafluoroethylene/vinylidene copolymer (THV), or perfluoro(1-butenyl vinyl ether) homocyclopolymer having functionalized polymer-end groups.

31. The method according to one of any paragraphs 24 to 30, wherein the outer elastomer layer and the innert fluoropolymer layer are adhered together by bonding.

32. The method according to paragraph 31, wherein the bonding is by chemical bonding, adhesive bonding, thermal fusion bonding, solvent bonding, laser welding, and surface treatment, extrusion, co-extrusion, coating, lamination, or combinations thereof.

33. The method according to one of any paragraphs 23 to 32, wherein the container comprises a bag, flask, or tube.

34. The method according to paragraph 33, wherein the bag, flask, or tube contains at least one sealable access port.

35. The method according to paragraph 23, wherein steps a) and b) are interchangeable.

36. The method according to paragraph 23, further comprising the step of incubating the container.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Tested Samples

TABLE 1

TOC data

| Material | Form | Extraction Conditions | TOC (TOC-Blank) |
|---|---|---|---|
| PMP Film | Film | 70° C., 24 hours, 3 cm$^2$/mL | 0.07 ppm (0.00001 mg/cm$^2$) |
| Primed Thermoset Silicone/1 mil FEP Laminate | Bag with Laminate as bottom sheet | 70° C., 24 hours, 3 cm$^2$/mL | 0.02 ppm (0.00001 mg/cm$^2$) |
| Unprimed Thermoset Silicone/1 mil FEP Laminate | Bag with Laminate as bottom sheet | 70° C., 24 hours, 3 cm$^2$/mL | 0.01 ppm (0.000003 mg/cm$^2$) |
| PMP/1 mil FEP Laminate | Bag with Laminate in cut-out bag form (i.e. portion of bottom sheet) | 70° C., 24 hours, 3 cm$^2$/mL | 0.01 ppm (0.000003 mg/cm$^2$) |
| Thermoplastic Silicone/1 mil FEP Laminate (with liner) | Bag with Laminate in cut-out bag form (i.e. portion of bottom sheet) | 70° C., 24 hours, 3 cm$^2$/mL | 0.36 ppm (0.0001 mg/cm$^2$) |
| Thermoplastic Silicone/1 mil FEP Laminate (without liner) | Bag with Laminate in cut-out bag form (i.e. portion of bottom sheet) | 70° C., 24 hours, 3 cm$^2$/mL | 3.59 ppm (0.001 mg/cm$^2$) |
| FEP "Incumbent" | 2PF-0290 FEP Bag | 70° C., 24 hours, 3 cm$^2$/mL | 0.30 ppm (0.0001 mg/cm$^2$) | ppm = mg/L

Example 2

Dissolved Oxygen Experiments

An incumbent FEP bag made from 5 mil FEP on top and bottom a and a prototype bag made from 5 mil FEP on top and thermoplastic silicone/FEP on the bottom were filled to 300 mL and 190 mL respectively with tap water. These volumes correlate to a 1 cm thickness of water in the bag when it is lying flat, a recommendation that is well-known in industry. A port was cut out of each bag in order to feed in a nitrogen line to purge the water in the bag to a level below saturation. Dissolved oxygen (DO) levels were monitored using the PreSens probe affixed to the outside of the bag and aligned with the sensor dot on the inside of the bag. When the DO levels in the water reached a reasonably low value (~6-8%), the nitrogen line was removed from the bag and the port opening was clamped shut. The bag and rack were returned to a horizontal resting position for the remainder of the experiment. The PreSens probe was programmed to take DO measurements at designated time points in order to measure the ingress of oxygen as a function of time. It was assumed that the only path for oxygen ingress was through the walls of the bags.

Figure 3:
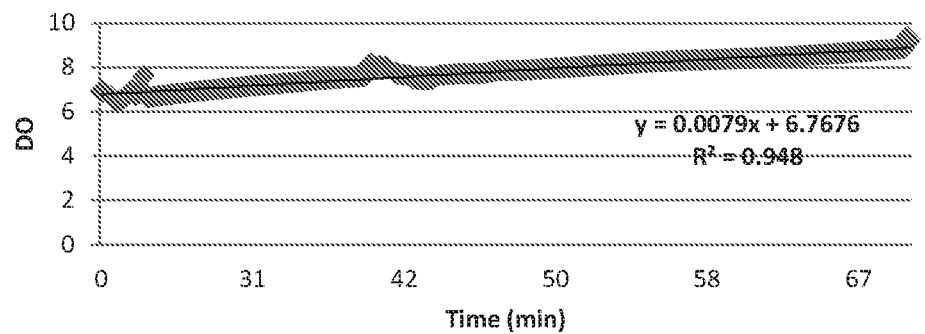
FIG. 3 shows a graphical representation of the initial ingress of oxygen into incumbent FEP bag.
Figure 4:
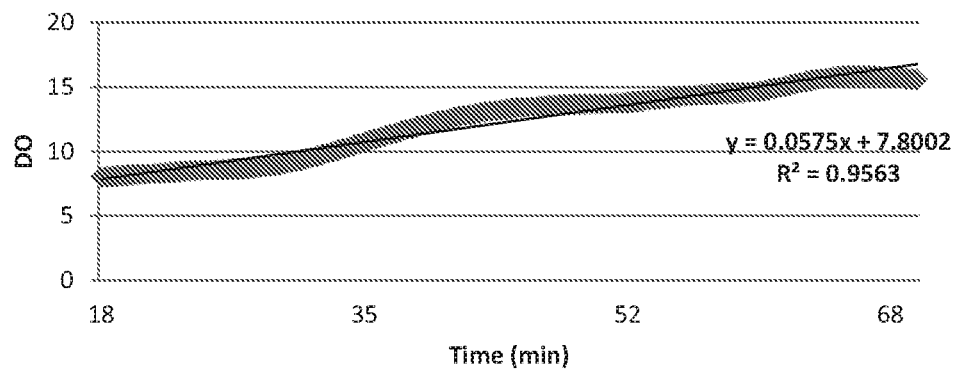
FIG. 4 shows a graphical representation of the initial ingress of oxygen in prototype bag with gas permeable laminate.
Figure 5:
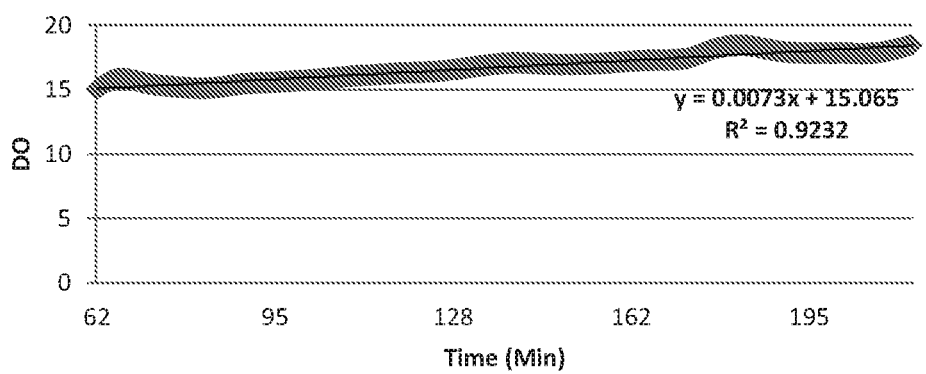
FIG. 5 shows a graphical representation of the approach to equilibrium in prototype bag made with gas permeable laminate.

Results:

Measurements from the PreSens system were downloaded and plotted in Excel for both bags (FIGS. 3, 4, and 5). The data was studied and observations were made to bracket the data. For instance, for the prototype bag, the beginning measurements were excluded because the bag was moved and manipulated in order to remove an air bubble from above the sensor. Also, because a longer measurement was taken for the prototype bag, the data was split into two linear sections, "Initial Ingress" and "Approach to Equilibrium". Due to this, the best comparison to make with the current data available is between FIG. 3 and FIG. 4 which demonstrate the initial ingress of oxygen into each of the bags as a function of time when starting at similar DO levels (~6-8%) for a similar amount of time (~68-70 min). Looking at FIG. 3 and FIG. 4, the comparison of slopes can be made to understand the difference in rate of ingress between the incumbent and prototype bags. The incumbent bag as a rate of 0.008% DO/min while the prototype bag has a rate of 0.06% DO/min, a difference of over 7x. This alludes to the positive impact of the more permeable material on the ingress of oxygen.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. An oxygen-permeable film comprising:
   a first polymer layer having a thickness in the range of about 0.01 mm to about 5 mm, the first polymer layer being a silicone layer; and
   a second fluid contact layer having a thickness in the range of about 0.01 mm to about 0.1 mm, the second fluid contact layer being an FEP layer,
   wherein the first polymer layer and the second fluid contact layer are adhered together, and
   wherein the oxygen permeable film has an oxygen permeability of at least 2000 cc/m$^2$ per day.

2. The oxygen-permeable film according to claim 1, wherein the first polymer layer has a thickness in the range of 0.1 to 1 mm.

3. The oxygen-permeable film according to claim 1, wherein the first polymer layer is a layer of cured liquid silicone rubber.

4. The oxygen-permeable film according to claim 1, wherein the first polymer layer is a layer of high consistency rubber.

5. The oxygen-permeable film according to claim 1, wherein the FEP layer has a thickness in the range of 0.01 to 0.04 mm.

6. The oxygen-permeable film according to claim 1, wherein a primer is used in the adhesion of first polymer layer to the FEP layer.

7. The oxygen-permeable film according to claim 1, wherein the FEP layer is C-treated at a surface adhered to the first polymer layer.

8. The oxygen permeable film according to claim 1, wherein the FEP layer is C-treated at a surface adhered to the first polymer layer, wherein the first polymer layer is a layer of cured liquid silicone rubber, and wherein a primer is used in the adhesion of first polymer layer to the FEP layer.

9. The oxygen-permeable film according to claim 1, wherein the FEP layer is treated at a surface adhered to the first polymer layer with a treatment selected from corona discharge, plasma treatment, etching, and combinations thereof.

10. The oxygen-permeable film according to claim 1, wherein FEP layer has a TOC in water of less than 0.1 mg/cm$^2$.

11. An oxygen-permeable container comprising an oxygen permeable film that comprises:
    an outer polymer layer having a thickness in the range of about 0.01 mm to about 5 mm, the outer polymer layer being a silicone layer; and
    an inner fluid contact layer having a thickness in the range of about 0.01 mm to about 0.1 mm, the inner fluid layer being an FEP layer,
    wherein the outer polymer layer and the inner fluid contact layer are adhered together, and
    wherein the oxygen permeable film has an oxygen permeability of at least 2000 cc/m$^2$ per day.

12. The container according to claim 11, wherein the container is in the form of a bag, flask, or tube.

13. The container according to claim 11, wherein the container is in the form of a cell culture bag comprising the oxygen-permeable film as a wall thereof.

14. The container according to claim 11, wherein the outer polymer layer has a thickness in the range of 0.1 to 1 mm.

15. The container according to claim 11, wherein the outer polymer layer is a layer of cured liquid silicone rubber.

16. The container according to claim 11, wherein the outer polymer layer is a layer of cured high consistency rubber.

17. The container according to claim 11, wherein the FEP layer has a thickness in the range of 0.01 to 0.04 mm.

18. The container according to claim 11, wherein a primer is used in the adhesion of outer polymer layer to the FEP layer.

19. The container according to claim 11, wherein the FEP layer is C-treated at a surface adhered to the outer polymer layer.

20. The container according to claim 11, wherein the FEP layer is C-treated at a surface adhered to the outer polymer layer, wherein the outer polymer layer is a layer of cured liquid silicone rubber, and wherein a primer is used in the adhesion of outer polymer layer to the FEP layer.

21. The container according to claim 11, wherein the FEP layer is treated at a surface adhered to the first polymer layer with a treatment selected from corona discharge, plasma treatment, etching, and combinations thereof.

22. The container according to claim 11, wherein the container comprises at least one sealable access port.

23. The container according to claim 9, wherein the inner fluid contact layer has a TOC in water of less than 0.1 mg/cm$^2$.

24. A method to cultivate cells in an oxygen permeable container according to claim 11, the method comprising:
 a) adding media and cells to the container; and
 b) incubating the container.

* * * * *